United States Patent [19]

Donzis

[11] Patent Number: 5,223,491
[45] Date of Patent: Jun. 29, 1993

[54] METHOD FOR REVITALIZING SKIN BY APPLYING TOPICALLY WATER INSOLUBLE GLUCAN

[76] Inventors: Byron A. Donzis, 3008 Rodgerdale, Houston, Tex. 77042;

[21] Appl. No.: 435,032

[22] Filed: Nov. 9, 1989

[51] Int. Cl.$^5$ .................... A61K 31/70; A61K 35/72; A61K 35/78; C12N 1/16
[52] U.S. Cl. .................................... 514/54; 424/520; 424/195.1; 435/255; 435/911
[58] Field of Search ............... 514/54; 424/195.1, 520; 435/255, 911

[56] References Cited

U.S. PATENT DOCUMENTS

| | | | |
|---|---|---|---|
| 4,138,479 | 2/1979 | Truscheit et al. | 424/92 |
| 4,182,751 | 1/1980 | Ayme | 424/92 |
| 4,337,243 | 6/1982 | Ayme | 424/92 |
| 4,343,784 | 8/1982 | Massot et al. | 424/45 |
| 4,695,549 | 3/1986 | Grabitz | 435/267 |
| 4,739,046 | 4/1988 | Di Luzio | 536/117 |
| 4,761,402 | 8/1988 | Williams | 514/54 |
| 4,818,752 | 4/1989 | Williams | 514/54 |
| 4,833,131 | 5/1989 | Williams | 514/54 |
| 4,992,540 | 2/1991 | Jamas et al. | 435/255 |
| 5,019,391 | 5/1991 | Bunte et al. | 435/255 |
| 5,037,972 | 8/1991 | Jamas et al. | 435/255 |
| 5,082,936 | 1/1992 | Jamas et al. | 435/255 |

OTHER PUBLICATIONS

Konishi, H., et al. *Chemical Abstracts*, 101:1988.
Burgolata and Golde, *Cancer Research*, 37:1739-1742, 1977 "Effect of Glucan on Granulopoiesis and Macrophage Genesis in Mice".
Czop, *Pathology and Immunopathology Research*, 5:286-296, 1986 "The Role of β-Glucan Receptors on Blood and Tissue Leukocytes in Phagocytosis and Metabolic Activation".
Kaplan, *Archives of Surgery*, 119:1005-1008, 1984 "Acceleration of Wound Healing by a Live Yeast Cell Derivative".
Goodson, *Journal of Surgical Research*, 21:125-129, 1976 "Augmentation of Some Aspects of Wound Healing by a Skin Respiratory Factor".
Hassid, et al., *Journal of the American Chemical Society*, 63:295-298, 1941 "The Molecular Constitution of an Insoluble Polysaccharide from Yeast Saccharomyces cerevisiae".
Manners, et al., *Journal of General Microbiology*, 80:411-417, 1974 "The Heterogeneity of Glucan Preparations from the Walls of Various Yeasts".
Leibovich and Danon, *Journal of Reticuloendothelial Society*, 27:1-11, 1980 "Promotion of Wound Repair in Mice by Application of Glucan".
Sauder, *Dermatologic Clinics*, 4:447-454, 1986 "Effect of Age on Epidermal Immune Function".
Uitto, *Dermatologic Clinics*, 4:433-446, 1986 "Connective Tissue Biochemistry of the Aging Dermis".

Primary Examiner—Douglas W. Robinson
Assistant Examiner—Susan M. Weber
Attorney, Agent, or Firm—Pravel, Hewitt, Kimball & Krieger

[57] ABSTRACT

A method revitalizing skin by applying topically a substantially purified water insoluble glucan, extracted from yeast cell walls, dispersed within a carrier. Also, disclosed is a method for producing the water insoluble glucan.

10 Claims, 2 Drawing Sheets

METHOD FOR REVITALIZING SKIN BY APPLYING TOPICALLY WATER INSOLUBLE GLUCAN

FIELD OF THE INVENTION

The present invention relates to a method for producing an insoluble extract of yeast, a composition comprising an insoluble yeast extract, and a method of use of an insoluble yeast extract.

BACKGROUND OF THE INVENTION

Glucan extracted from yeast cell walls is known to be a potent stimulator of the immune system. Numerous studies have indicated that in vivo administration of glucan significantly modifies host resistance to a wide variety of infectious diseases induced by bacterial, fungal, viral and parasitic organisms (DeLuzio, Trends in Pharmacological Science 4:344–347, 1983). Glucan has also been shown to have potent antitumor activity (DeLuzio et al Advances and Experimental Medicine and Biology 21A:269290, 1979).

The mechanism by which glucan exerts its beneficial effects is by interraction with specific glucan receptors located on macrophage cells (Czop, Pathology & Imnunipathology Research, 5:286–296, 1986). Langerhans cells are specialized macrophage cells located in the skin which function in an analagous manner as macrophages.

The general method for the production of glucan from yeast involves extraction with alkali followed by extraction with acid (Hassid et al, Journal of the American Chemical Society, 63:295–298, 1941). This method is time consuming, laborious and expensive to execute. It would be of great utility therefore to provide a method for the production of yeast glucan which can be accomplished in a shorter period of time which is inexpensive and easy to execute and which produces a glucan product which is capable of inducing the activities of macrophages and Langerhans cells. Most desirable would be a product capable of inducing Langerhans cell activity upon topical application to the skin.

It would be further desirable if such method produced a substantially protein-free extract of Saccharomyces, or Baker's yeast, exhibiting acceptable color and odor.

SUMMARY OF THE INVENTION

A simple, quick, efficient and inexpensive method for producing glucan from yeast, this method may be executed in approximately eight (8) hours time prior to drying. The method of this invention primarily differs from that of previous preparation methods in that yeast material is first autoclaved in an alkali solution, followed by an acid extraction and ethanol wash. In one embodiment of the invention, the product is ground to a particle size of one micron or less. This method produces a particularly potent insoluble glucan product which is substantially free of protein and non-glucose sugars, and which significantly stimulates the activities of macrophages. The product is produced with negligible odor and little color, and is substantially protein-free.

DETAILED DESCRIPTION OF THE PREFERRED EMBODIMENTS

Figure 1:
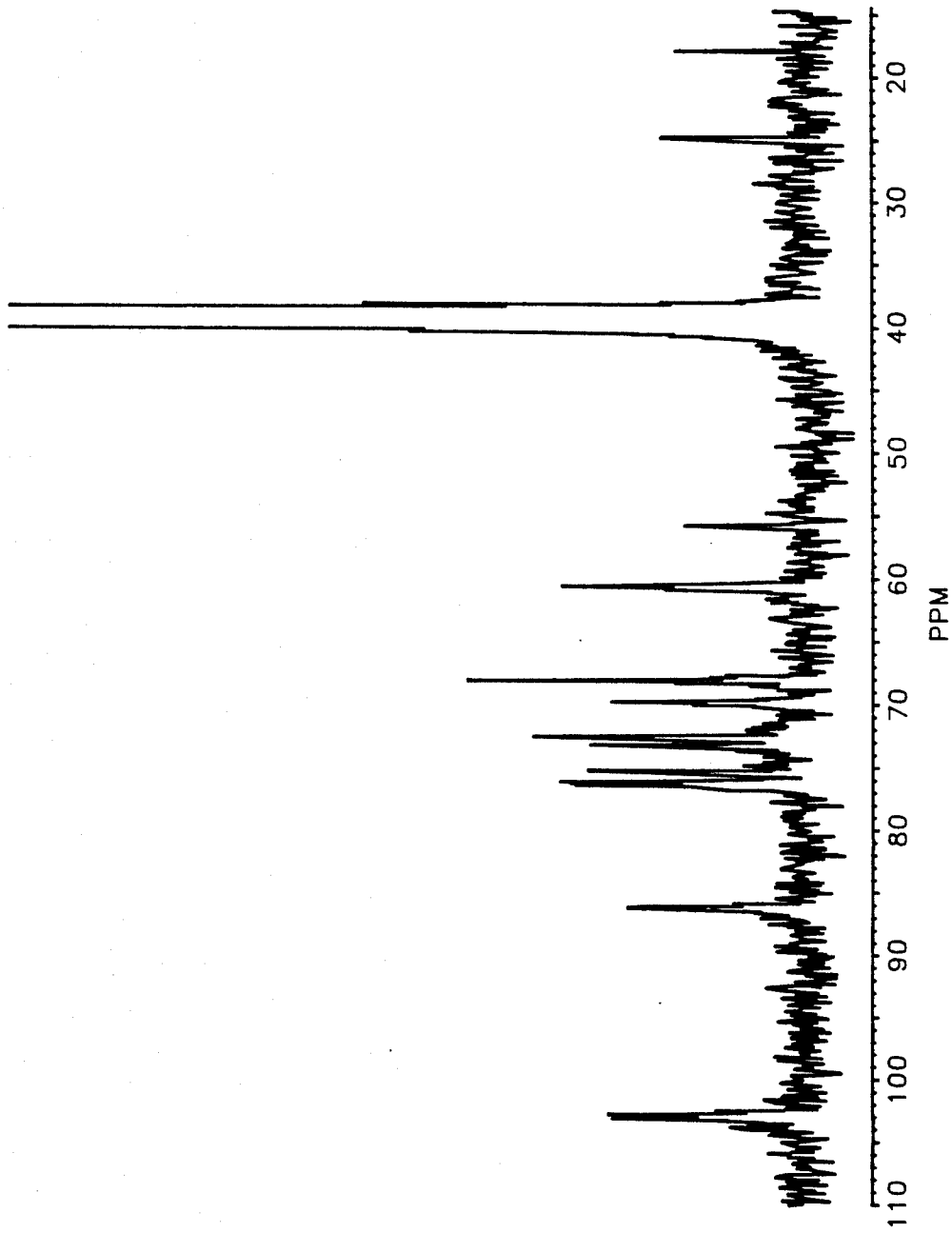
FIG. 1 is a carbon-13 nuclear magnetic resonance (NMR) spectrum of glucan prepared by the method of the present invention.

Yeast cells may optionally be sonicated or otherwise broken to prepare a yeast cell wall material prior to extraction. The preferred yeast is that of the genus Saccharomyces and most preferably Saccharomyces cerevisiae including Baker's yeast and Brewer's yeast. The most preferred is Baker's yeast. Yeast cells or yeast cell walls are then autoclaved in an alkaline solution. The preferred alkali is sodium hydroxide in the range of 0.5 to 3.0 normal. Most preferred is 1.5 normal sodium hydroxide. Dry yeast or yeast cell wall material is mixed in the alkali solution and then autoclaved for a period of time ranging from 15 minutes to 1.5 hours, preferably for 30 minutes to one hour. The pressure within the autoclave is preferably approximately 15 psi. The mixture is permitted to cool, preferably with stirring for approximately 15 minutes and is then centrifuged at approximately 5,000 times×g (gravity force) for about 15 minutes to pellet the alkaline insoluble residue. The supernatant liquid is removed and the pellets are resuspended and washed with distilled water. The residue is then pelleted by centrifugation at 5,000×g for approximately 15 minutes. This water washing step may be repeated from 1 to 3 times.

The water washed pellets are resuspended in an acid solution. This acid may be for example, glacial acetic acid or hydrochloric acid, and preferably is acetic acid. The most preferred acid solution is approximately 3% glacial acetic acid. The water washed pellets are stirred into the acidic solution which may be prewarmed. The acid solution is then heated to approximately 85° C. for a period of time ranging from about 30 minutes to about 3 hours. Preferably this period of time is one hour. The acid mixture is then centrifuged as described above to pellet the acid insoluble residue.

The pellets may again be washed with water as described above from one to three times, saving the residual pellets and discarding the supernatant liquid with each wash.

The acid insoluble residue is then washed with a 100% ethanol, saving the solid residual material and discarding the supernatant liquid.

Optionally, the acid insoluble residue may be washed with acetone either prior to or following the ethanol wash step. If the ethanol wash is followed by the acetone wash, it may be useful to again wash with ethanol from one to three times following the acetone wash.

The residual material which has been washed in ethanol or acetone is then dried. This drying may be air drying at room temperature or be assisted by use of vacuum or other drying methods and is continued until a constant weight of the glucan product is reached.

Glucan may be prepared by these methods, or may be purchased commercially from ImmunoDyne, Inc. (Palo Alto, Calif.).

Characteristics of Glucan

Purified glucan prepared by the method of this invention is essentially protein and endotoxin-free, and is comprised of polyglucose having predominantly β1-3 glycosidic linkages. More specifically, the glucan product is free from other, non-glucose sugars, is comprised of at least 35% carbon, less than 0.01% phosphorous and less than 0.20% nitrogen as determined by elemental analysis. The molecular weight is approximately less than 250,000, and may be less than 70,000. The specific active fragment may be at least 7 glucose residues of approximately 1000-1500 molecular weight.

Preparation of Topical Compositions Comprising Specific Yeast Polysaccharides Glucan may be utilized in powdered form, or prepared as a suspension a carrier suitable for topical application to the skin. Carrier compositions suitable for topical application to the skin would include for example creams, lotions, and ointments.

Compositions comprising glucan may also contain moisturizers or agents to enhance entry of the compound into the skin, agents to enhance retention to the product on the skin, fragrance, color, and the like. Glucan may also be added to commercially available skin care products to provide skin revitalizing and repair characteristics to the product.

Specifically, the revitalizing and repair characteristics of the present invention include thickening the skin, reducing the number, depth, and length of winkles, inducing the synthesis of collagen and elastin, inducing the proliferation and activity of macrophages and Langerhans Cells, inducing the number and activity of fibroblasts, reducing redness, irritation, and roughness of the skin, and reducing the number and size of skin lesions.

By way of example, a moisturizing lotion comprising the glucan may be further comprised of the following: water, propylene glycol, avocado oil, isocetyl stearate, octyl methoxy cinnamate, polysorbate 60, maleated soy bean oil, stearic acid, silicone fluid, cetyl acetate, vitamin E acetate, glyceryl monostearate, propylene glycol monostearate, sorbitan stearate, vitamin A palmitate, benzophenone-3, silicone wax, triethanolamine, diazolidinylurea, methylparaben, lanolin alcohol, disodium edetate, carbomer 934, and propylparaben.

The term "skin" is used herein to refer to the protective outer covering of the body, including the scalp and hair follicles, the lining of the eye, mouth, ear, nose, and the like. Such skin is comprised of stratified layers of cells in which are located the immunogenic macrophages or Langerhans cells which are the target of the active ingredient of the products of this invention. It is expected that a product which is effective in the treatment of facial skin will be effective in the treatment of skin of the scalp, hair follicle, ear, nose, mouth and the like.

Glucan may be added to skin creams, cosmetics, ointments, and lotions; to shaving creams and after shave lotions; to soaps, shampoos, conditioners, hair sprays; to suntan oils and lotions; to dry skin, wound-treatment, and acne-treatment creams and medicants; to deodorants and douches; to toothpastes, mouth washes, and dental amalgams; to nose drops, nasal sprays, and ear drops; to eye washes and eye drops; and to additional lotions, creams, solutions and the like which directly contact the skin.

The amount of the glucan to be used, and the specific components of a composition will depend upon the nature of the product and its intended use. Generally, the effective amount of glucan will be from about 0.02 to about 10 mg/oz, preferably from about 0.5 to about 2.5 mg/oz, and most preferably from about 1 to about 2.5 mg/oz.

EXAMPLES

Example 1

Preparation of Yeast Extract in the Absence of Acetone 500 grams of dried Baker's yeast was added to 2.4 liters of warm (50° to 60° C.), 1.5 normal sodium hydroxide while stirring. The mixture was stirred until the yeast was thoroughly dispensed. The mixture was then autoclaved for 30 minutes at approximately 15 psi. After cooling to room temperature, the mixture was centrifuged at 5,000×g for 15 minutes. The supernatant was removed and the pellets were resuspended with vigorous stirring in a total of one liter of distilled water. The water mixture was centrifuged at 5,000×g for 15 minutes and the supernatant was removed. This water-wash was repeated two times for a total of three water-washes.

The washed pellet was resuspended in two liters of 3% glacial acetic acid and heated at 85° C. for one hours. The acid mixture was then centrifuged as described above and the supernatant removed. The pellet was washed with a total of one liter of distilled water, as described above. The supernatant was removed and the pellets were resuspended in a total of one liter of absolute ethanol. The residue was again centrifuged as described above. The ethanol wash was repeated one time for a total of two ethanol washes and the pellet then resuspended in 0.5 liters of absolute ethanol. The ethanol mixture was filtered on a glass fiber filter in a Buchner funnel pressing out the residual ethanol. The filter cake produced from the Buchner funnel was spread out on a large glass dish and air dried from 4 to 5 hours, periodically breaking up any lumps. The precipitate was dried at 40° C. under a vacuum while continuing to break up any lumps. This material was dried at 40° C. under vacuum for approximately 24 hours or until a constant weight was reached. The yield of this extraction material was approximately 50 grams.

Example 2

Preparation of Yeast Glucan Using Acetone

Approximately 200 grams of Brewer's yeast was dispersed in one liter of 1.5 normal sodium hydroxide. The mixture was stirred until homogeneous then autoclaved as described for Example 1 for one hour. The autoclaved material was centrifuged at 3,000×g for 15 minutes, discarding the supernatant and retaining the alkaline insoluble residue. The alkaline insoluble residue was washed three times, each wash consisting of one liter of distilled water with centrifugation at 3,000×g for 15 minutes to pellet the solid material and discarding the supernatant liquid. The water-washed residue was then stirred into warm (85° C.) 3% acetic acid solution and stirred for approximately 3 hours. The acid solution was then centrifuged one time as described above and the acid insoluble residue resuspended in one liter of distilled water. The washed acid insoluble residue was then resuspended in 600 milliliters of 100% ethanol. The solid residue was again pelleted by centrifugation at 3,000×g for 15 minutes. The ethanol-washed residue was resuspended in approximately 600 milliliters of acetone and again centrifuged at 3,000×g for 15 minutes. The acetone-washed residue was mixed with the residual acetone in the centrifuge tube and then was collected in a sintered glass funnel. The acetone was drawn from the glass funnel by vacuum. The collected solid material was scraped from the funnel into small Petri dishes. The Petri dishes were then placed into a desiccator and dried under vacuum. Clumps of dried material were broken up with a spatula and placed into a storage container.

Example 3

Preparation of Yeast Glucan

The method of Example 1 was followed with the exception that after acid extraction the water-washed acid insoluble residue was resuspended in one liter of acetone. The solid material was pelleted and the supernatant liquid discarded as described above. The acetone washed pellets were resuspended in a total of one liter of absolute ethanol and the method continued as described in Example 1. The yield from 500 grams of dried Baker's yeast was approximately 50 grams.

Example 4

Comparison of Yeast Extract Prepared by Prior Art Method With The Shorter Autoclave Method of The Present Invention Yeast extract was prepared according to the method of Manners et al *J. General Microbiology*, 80:411-417, 1974. According to this method, yeast was heated to approximately 50-60° C. in 1.5 normal sodium hydroxide for three hours. The heated yeast mixture was diluted with distilled water and then centrifuged to pellet the insoluble residue. The insoluble residue was resuspended in 0.75 normal sodium hydroxide and left standing at room temperature for 18 hours.

After 18 hours the alkaline solution was diluted with distilled water and again centrifuged to pellet the insoluble residue. The insoluble pellets were resuspended in distilled water and heated to 80° C. The pH of this solution was then made acidic by the addition of acetic acid and then centrifuged to pellet the insoluble material. The residual pellet was then resuspended in 0.75 normal sodium hydroxide and heated to 80° C. for two hours. This solution was diluted with distilled water and then the pH adjusted to approximately 4.5 by the addition of acetic acid. This acidic solution was again centrifuged to pellet the insoluble material. The residual pellet was resuspended in hot water at a temperature of 80° C. The hot water solution was centrifuged to pellet the residual insoluble residue which was then resuspended in 0.5M acetic acid and heated to between 70° C. and 80° C. for one hour. The heated acid solution was diluted with distilled water and heated to 80° C. for one hour. The diluted acid solution was then centrifuged to pellet the insoluble residual material. The acid heating and diluting step was repeated. The diluted acid solution was centrifuged to pellet the insoluble material. The insoluble pellet was then resuspended in 0.02M sodium acetate and autoclaved for one hour. The autoclaved material was then centrifuged to pellet the insoluble material. The insoluble pellet was washed six times with distilled water each time centrifuging to pellet the insoluble material. After the sixth water wash, the insoluble pellet was resuspended to 0.01M sodium acetate and autoclaved for forty minutes. The autoclaved material was washed three times with distilled water, centrifuging between each wash to pellet the insoluble material. The insoluble washed pellet was resuspended in distilled water and autoclaved for forty minutes. The autoclaved material was then stirred for eighteen hours at room temperature in distilled water. The water solution was then centrifuged to pellet the insoluble residual material. The insoluble material was washed with 100% ethanol three times centrifuging with each wash and retaining the insoluble residual material. The ethanol washed pellet was then washed with acetone. The acetone solution was centrifuged to obtain the insoluble residue. The insoluble residue was then dried under vacuum.

The method of Example 2 was followed to produce yeast glucan by the shortened method of the present invention.

The product of the Manner's method was compared with the product of the shortened method of the present invention with respect to percent product yield, carbohydrate content, and protein content. The results are shown in Table I, and indicate that the shortened method provides a greater percent yield of product having a reduced protein content.

TABLE I

|  | % Yield | Carbohydrate (mg/10$^6$ particles) | Protein (mg/10$^6$ particles) |
|---|---|---|---|
| Prior Art Method (6-7 days) |  |  |  |
| 1 | 4.37 | 0.67 | 0.050 |
| 2 | 4.27 | 0.82 | 0.049 |
| 3 | 3.27 | 0.95 | 0.053 |
| Shortened Method (1 day) |  |  |  |
| 1 | 19.27 | 9.67 | 0.033 |
| 2 | 13.37 | 0.74 | 0.043 |

Example 5

Characteristics of Glucan Product

The water insoluble glucan product prepared as described for Example 1 was dissolved in dimethyl sulfoxide (DMSO) with an internal standard of tetramethylsilane (TMS). A carbon thirteen nuclear magnetic resonance (NMR) spectrum was run for 24-hours at 50° C. to obtain a highly resolved spectrum. An elevated temperature was necessary to maintain the glucan product in solution.

A complete list of peaks and intensities is shown in Table II. The spectrum was compared with an NMR of a standard β-(1-3) glucan as shown in Table III. The NMR spectrum of the glucan product includes peaks corresponding to those of β1-3 glucan. The resonance at 39.5 ppm is due to tetramethylsilane (TMS), an internal standard.

The NMR spectrum of the glucan product produced according to the method of Example 1 is shown in FIG. 1.

TABLE II

| C-NMR Analysis of Insoluble Glucan Product | | | | |
|---|---|---|---|---|
| # | Cursor | Frequency | PPH | Intensity |
| 1 | 16637 | 9578.984 | 105.7794 | 1.449 |
| 2 | 16818 | 9458.690 | 104.4510 | 1.528 |
| 3 | 16899 | 9405.430 | 103.8628 | 2.581 |
| 4 | 17002 | 9336.690 | 103.1038 | 5.922 |
| 5 | 17035 | 9315.267 | 102.8672*C1 | 6.008 |
| 6 | 17203 | 9203.493 | 101.6329 | 1.444 |
| 7 | 18447 | 8377.915 | 92.5161 | 1.462 |
| 8 | 18922 | 8062.757 | 89.0359 | 1.339 |
| 9 | 19318 | 7800.536 | 86.1402*C3 | 5.361 |
| 10 | 20477 | 7031.718 | 77.6503 | 1.353 |
| 11 | 20643 | 6921.481 | 76.4329 | 7.156 |

TABLE II-continued

C-NMR Analysis of Insoluble Glucan Product

| # | Cursor | Frequency | PPH | Intensity |
|---|--------|-----------|-----|-----------|
| 12 | 20672 | 6902.345 | 76.2216*C5 | 7.430 |
| 13 | 20786 | 6826.326 | 75.3822 | 6.567 |
| 14 | 21011 | 6677.016 | 73.7335 | 2.347 |
| 15 | 21071 | 6637.226 | 73.2940 | 6.604 |
| 16 | 21152 | 6583.452 | 72.7001*C2 | 8.179 |
| 17 | 21230 | 6531.804 | 72.1298 | 2.122 |
| 18 | 21539 | 6326.695 | 69.8648 | 5.955 |
| 19 | 21752 | 6185.499 | 68.3056*C4 | 0.039 |
| 20 | 22086 | 5963.948 | 65.8590 | 1.327 |
| 21 | 22436 | 5731.508 | 63.2922 | 1.350 |
| 22 | 22780 | 5503.357 | 60.7728*C6 | 7.325 |
| 23 | 23455 | 5055.718 | 55.8296 | 3.868 |
| 24 | 23571 | 4978.488 | 54.9767 | 1.541 |
| 25 | 25590 | 3639.622 | 40.1918 | 177.048 |
| 26 | 25621 | 3618.648 | 39.9602 | 485.046 |
| 27 | 25653 | 3597.659 | 39.7284 | 930.218 |
| 28 | 25684 | 3576.668 | 39.4966 | 1075.865 |
| 29 | 25716 | 3555.678 | 39.2649 | 913.363 |
| 30 | 25748 | 3534.675 | 39.0329 | 459.904 |
| 31 | 25779 | 3513.701 | 38.8013 | 155.146 |
| 32 | 25954 | 3398.177 | 37.5256 | 1.493 |
| 33 | 26115 | 3291.157 | 36.3438 | 1.528 |
| 34 | 26262 | 3193.637 | 35.2669 | 1.319 |
| 35 | 26671 | 2922.392 | 32.2716 | 1.375 |
| 36 | 26751 | 2868.834 | 31.6801 | 1.571 |
| 37 | 27157 | 2599.841 | 28.7097 | 1.892 |
| 38 | 27441 | 2411.497 | 26.6298 | 1.385 |
| 39 | 27632 | 2284.746 | 25.2301 | 4.547 |
| 40 | 27988 | 2048.312 | 22.6192 | 1.407 |
| 41 | 28583 | 1653.813 | 18.2628 | 4.086 |

TABLE III

Comparison of Selected Peaks from Insoluble Glucan Product of Example 1 With β-(1 → 3) Glucan Standard

| β-(1 → 3) Glucan | | Insoluble Yeast Extract | |
|---|---|---|---|
| Carbon | PPM | PPM | Intensity |
| C-1 | 102.45 | 102.87 | 6.008 |
| C-3 | 86.9 | 96.14 | 5.361 |
| C-5 | 76.10 | 76.22 | 7.430 |
| C-2 | 72.70 | 72.70 | 8.179 |
| C-4 | 68.27 | 68.31 | 10.039 |
| C-6 | 60.79 | 60.77 | 7.325 |

The insoluble glycan product prepared as described for Example 1 was hydrolyzed by two methods to characterize the sugar moieties of the product. In the first hydrolysis, the product was heated for 8 hours at 110° C. in 2M trifluoroacetic acid. In the second hydrolysis, the product was swelled in 72% trifluoroacetic acid for 16 hours at 40° C., then diluted to 5% trifluoroacetic acid, and hydrolyzed at 110° C. for 6 hours. After hydrolysis two internal standards were added to each sample; myo-inositol and i-erythriotol. These alditol acetate standards were prepared according to Metz, et a., (J. Metz, W. Ebert, and H. Weicher, *Chromotographia*, 4, (1970) 345-350). The samples were then analyzed by gas chromatography on a 10'×⅛" nickel 200 stainless steel column packed with 5% SP2340 on 70/80 mesh Supelcoport, using a flame ionization detector. The oven was held at 180° C. for two minutes with the temperature was programmed to increase at 2° C./minute up to 250° C.

The samples were compared to an external standard containing of the alditol acetate derivatives of arabinose, xylose, marnose, galactose, and glucose. Both hydrolyzates showed peaks corresponding only to glucose and the internal standards myo-inositol and i-erythritol.

The insoluble glucan product, was thus shown to be a glucan, or polyglucose containing no other sugar moiety.

The glucan product prepared according to the method of example 1 was subjected to elemental analysis.

Carbon (C) and hydrogen (H) analyses were determined by combustion on a Perkin Elmer 240 Elemental Analyzer.

Phosphorous (P) was determined colorimetrically by phosphomolybdate test.

Nitrogen (N) was determined by the Kjeldahl method. The percent protein was converted from the nitrogen value according to the Official Methods of Analysis of the Association of Official Analytical Chemists, Method 10.195, Thirteenth Edition, 1980.

TABLE IV

Elemental Analysis of Insoluble Glucan

| % C | % H | % P | % N | % PROTEIN |
|-----|-----|-----|-----|-----------|
| 38.81 | 6.87 | 0.0066 | 0.17 | 1.06 |

Example 6

Bioassay of Yeast Extract Material

Yeast extract was prepared as described for Examples 1 and 2. On day 0, each of three mice per test group was injected intraperitoneally with 20 mg/kg of the test material or with vehicle (phosphate buffered saline). On day 3, each animal was injected with 0.1 ml of a suspension of *Cryptococcus neoformans* (approximately $10^6/0.1$ ml). All animals were sacrificed 30 minutes after the microorganism injection.

The peritoneal cavity of each animal was lavaged and the peritoneal exudate cells from each suspension were washed. Each washed cell suspension was stained with acridin orange (0.1%) and observed for the number of macrophages which had injested the organisms. A total of 100 macrophages were counted per group and the average number of yeast per phagocytic macrophage was determined. The results are shown in Table V and indicate that the yeast extracts prepared by the methods as described in Examples 1 and 2 stimulated macrophage activity.

TABLE V

| Test Material | Number of Phagocytic Machrophages Mean (S.D.) |
|---|---|
| 1 Example 1 | 30.7 (9.0) |
| 2A Example 2 | 7.7 (4.0) |
| 2B Example 2 | 13.3 (8.6) |
| 3 Vehicle | 2.3 (1.5) |

Example 7

Preparation of Glucan

Brewers yeast was sonicated and centrifuged to yield cell wall material.

Figure 2:
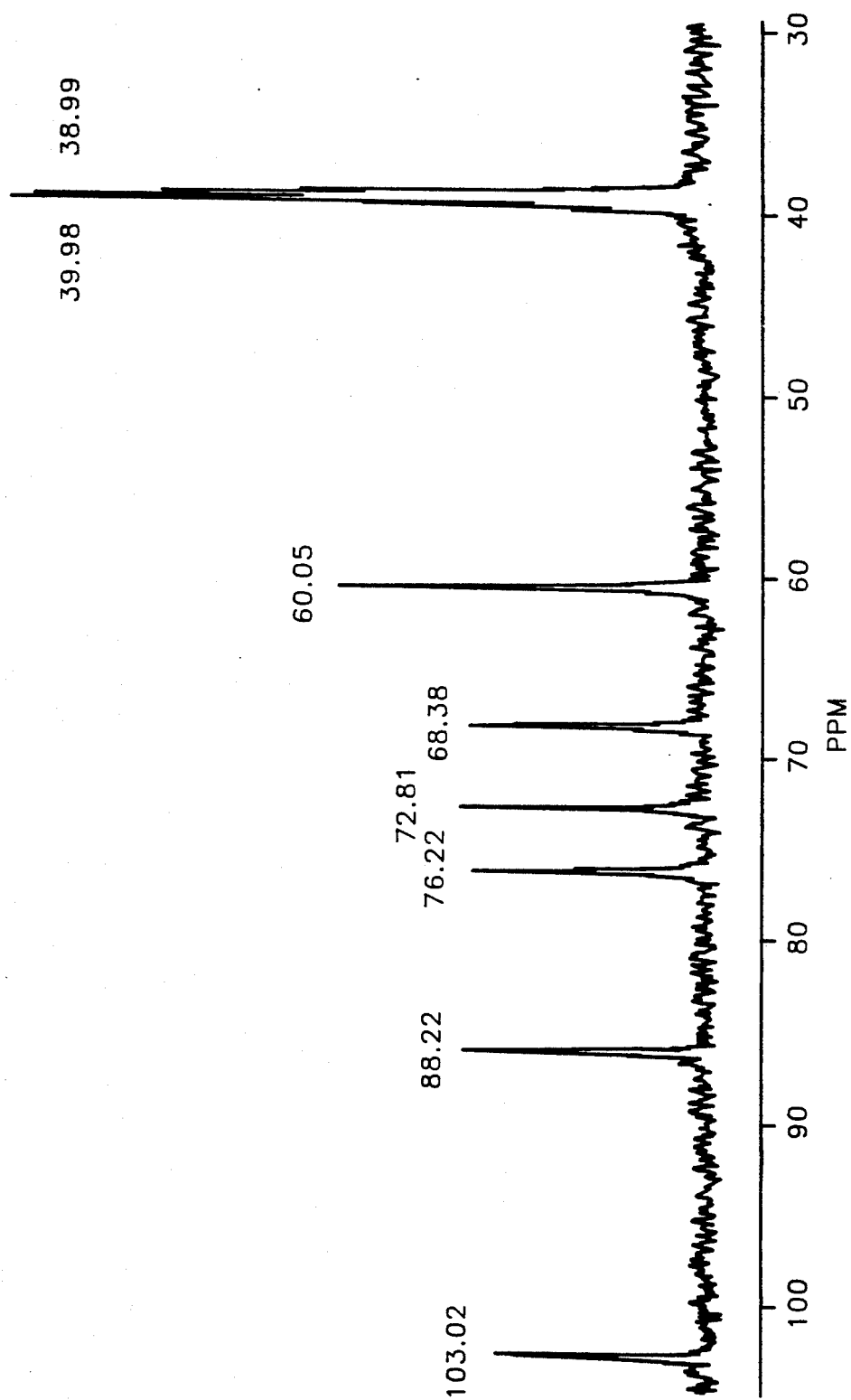
FIG. 2 is a carbon-13 NMR of glucan prepared by the method of Example 7.

Yeast cells wall material (40 pounds, 18.2 kg) containing approximately 15% solids was centrifuged to pellet the solid material. The resultant residue pellet was washed once each with 26%, 19%, and 14% hydrochloric acid. With each wash, the acid was added, the residue heated to 90°-93° C. while stirring, the stirred mixture allowed to cool and the cooled solution centrifuged. The acid-washed residue was then washed with 5 passes of water, repeating the procedure of adding the wash, heating while stirring, cooling, and then centrifuging. The residue was then washed with 4 passes of 100% ethanol, each pass consisting of a 24 hour period of stirring prior to centrifugation. The residue was then washed with 5 passes of water, each pass consisting of heating to 90°–93° C. while stirring, cooling, and then centrifuging. The residue was then suspended in a minimum volume of water and lyophilized. The expected yield was 10%, or 270 grams. The resultant extract was analyzed by nuclear magnetic resonance (NMR) as shown in FIG. 2.

Example 8

Activation of Macrophages by Glucan

Glucan extracted from yeast cell wall material as described in Example 7 was tested for its ability to stimulate macrophage activation in mice. Doses to 0.008, 0.04, 0.2. and 1.0 mg/kg body weight of the test compound in normal saline were administered by peritoneal injection, with normal saline carrier as control, to three animals per test group.

The activation of macrophages was determined in 2 ways: T-lymphocyte rosette formation and increased bactericidal activity against *Staphlococcus aureus* and *Streptoccoccus pneumonae*.

Rosette Formation:

Active macrophages in the peritoneal fluid stimulate the proliferation of T-lymphocytes. The resultant increase in T-lymphocytes was assayed by incubating mouse peritoneal exudate collected at 24, 72 and 144 hours post injection with chicken red blood cells. Red blood cells recognize and bind the surface of T-lymphocytes, resulting in "rosette" formation of red blood cells encircling the t-lymphocytes. These formations are easily recognized and counted under light microscopy. The number of rosettes produced using peritoneal fluid from mice treated with glucan was increased over that of the control as shown in Table VI. This increase in the number of T-lymphocytes indicated increased macrophage activity in glucan treated mice.

Bacterial Activity:

Twenty minutes prior to the collection of peritoneal exudate at 24, 72, and 144 hours post injection, the animals received i.p. injections of *S. aureus*. After collection of peritoneal extrudate, the macrophages is the fluid were examined under a microscope for evidence of phagocytosis. Macrophages phagocytosing more than 3 bacteria were considered bactericidal. One hundred macrophages were observed for each sample. The results were expressed as the percentage of bactericidal macrophages, and are shown in Table VII.

Glucan was effective in stimulating and activating macrophages even at very low doses of 0.04 mg/kg, as shown in Table VI and VII.

TABLE VI

| Dose Glucan | % Rosette Formation | | |
|---|---|---|---|
| | Time post injection (hours): | | |
| (mg/kg) | 24 | 72 | 144 |
| 0 | 8 | 7 | 3 |
| 0.008 | 8 | 8 | 1 |
| 0.04 | 7 | 11 | 6 |
| 0.20 | 6 | 17 | 8 |
| 1.00 | 8 | 18 | 8 |

TABLE VII

| Dose Glucan | % Macrophages With Bactericidal Activity | | |
|---|---|---|---|
| | Time post injection (hours): | | |
| (mg/kg) | 24 | 72 | 144 |
| 0 | 1 | 2 | 1 |
| 0.008 | 3 | 4 | 2 |
| 0.04 | 6 | 4 | 7 |
| 0.20 | 28 | 24 | 29 |
| 1.00 | 36 | 25 | 26 |

Example 9

Reduced Skin Irritation, Roughness, and Redness Using After Shave Lotion Comprising Glucan A suspension of glucan (0.5 or 2.5 mg/oz) was prepared by adding solid glucan prepared as described in Example 7 to a commercially available after shave lotion. Ten male subjects, aged 25 to 55, free of any systemic or dermatological disease and all self-described as having sensitive skin participated in the study. Subjects were instructed not to use any cosmetic or medicinal preparations on their faces for a period of one week prior to the study. On day one of the test, the subjects were randomly assigned to test products to the right or left sides of their faces, with the left side serving as control. The subjects shaved each side of their faces at home daily, following their normal shaving regimen. After shaving, the face was rinsed with tap water, and patted dry with a towel. After the face was patted dry, each test product was shaken to disperse the insoluble yeast extract and applied to the appropriate side of the face. Clinical evaluation was made at 2 and 4 weeks of the study.

Subjects were asked a series of questions about their skin and product differences. Faces were clinically evaluated for erythema or irritation, roughness, and nicks and cuts, and graded on a scale of 0 (absent) to 3 (maximum). The data are shown in Table VIII.

The use of the lotion containing glucan reduced erythema and irritation of the face, greatly reduced the rough appearance of the skin, and reduced the number of nicks and cuts.

TABLE VIII

| | Glucan Aftershave | | | | | |
|---|---|---|---|---|---|---|
| | Irritation | | Roughness | | Nick/cuts | |
| Subject | Control | Glucan | Control | Glucan | Control | Glucan |
| 1 | 0 | 1.5 | 1 | 0 | 1 | 0/5 |
| 2 | 1 | 0.5 | 1 | 0 | 0 | 0 |
| 3 | 1 | 0.5 | 1 | 0 | 0 | 1 |
| 4 | 0 | 0 | 0 | 0 | 3 | 1 |
| 5 | 0 | 0 | 1 | 0 | 0 | 0 |
| 6 | 0 | 0 | 1 | 0 | 0.5 | 0 |
| 7 | 0.5 | 0.5 | 1 | 0 | 1 | 0.5 |
| 8 | 1 | 0.5 | 1 | 0 | 1.5 | 1 |
| 9 | 1.5 | 0.5 | 1 | 0 | — | — |
| 10 | 2 | 1 | 1 | 0.5 | — | — |
| Total | 7.0 | 5.0 | 9.0 | 0.5 | 9.5 | 4.0 |

Key
0 - None
1 - Minimum
2 - Moderate
3 - Marked

Example 10

Reducing Wrinkles With Skin Cream Comprising Glucan

The subject of this study was a 57-year-old male. Daily, after shaving, from May, 1987 through March, 1988, the subject applied the skin cream containing glucan described for Example 7 to his face. Once or twice each month, the subject also used an apricot facial scrub. Direct observations and comparative photographs spanning nine months demonstrated a definite change in appearance. Wrinkles at the corners of the eyes were substantially reduced and the skin had a more supple look. No peeling, irritation or redness was noted.

Example 11

Reduced Skin Lesions, Cracks and Dryness With Skin Cream Comprising Glucan

The subject, a female of approximately 60 years of age, had complained of painful lesions of the backs of her hands and between her fingers for approximately 18 months. Her condition was diagnosed by several dermatologists as eczema or dermatitis of the atopic variety. None of the prescribed treatment creams alleviated her symptoms. The skin cream described for Example 10 containing 2.5 mg/oz of glucan was applied to the lesions three times daily. After three days, the subject described a tingling feeling in the lesions. After approximately ten days, noticeable improvement had occurred in the appearance of the subject's skin. After three weeks, the lesions had healed, but for a few between the fingers, and these showed considerable improvement.

Having described the invention above, various modifications of the techniques, procedures, material and equipment will be apparent to those in the art. It is intended that all such variations within the scope and spirit of the appended claims be embraced thereby.

We claim:

1. A method for revitalizing skin, comprising:
   applying topically to said skin a composition comprising:
   a carrier suitable for topical application to the skin; and
   a substantially purified water insoluble glucan extracted from yeast cell walls dispersed within said carrier in an amount of from about 0.1 mg per ounce to about 10 mg per ounce, wherein said revitalizing is selected from the group consisting of: reducing the number, depth or length of wrinkles of the skin, thickening of the skin, reducing irritation of the skin, reducing roughness of the skin, reducing redness of the skin, and reducing dryness of the skin.

2. The method of claim 1, wherein said amount of glucan is from about 0.5 to about 2.5 milligram per ounce.

3. The method of claim 2, wherein said amount of glucan is from about 1 to about 2.5 milligram per ounce.

4. The method of claim 1, wherein said revitalizing is reducing the number, depth or length of wrinkles of the skin.

5. The method of claim 1, wherein said revitalizing is thickening of the skin.

6. The method of claim 1, wherein said revitalizing is reducing irritation of the skin.

7. The method of claim 1, wherein said revitalizing is reducing roughness of the skin.

8. The method of claim 1, wherein said revitalizing is reducing redness of the skin.

9. The method of claim 1, wherein said revitalizing is reducing dryness of the skin.

10. The method of claim 1, wherein said glucan is polyglucose having predominantly beta 1-3 glycosidic linkages.

* * * * *